US011045539B2

(12) United States Patent
Le Gouellec et al.

(10) Patent No.: US 11,045,539 B2
(45) Date of Patent: Jun. 29, 2021

(54) ATTENUATED STRAIN OF PSEUDOMONAS AS A VACCINE FOR PSEUDOMONAS INFECTION

(71) Applicants: UNIVERSITÉ GRENOBLE ALPES, St. Martin d'Hères (FR); CENTRE HOSPITALIER UNIVERSITAIRE GRENOBLE ALPES, La Tronche (FR); ETABLISSEMENT FRANÇAIS DU SANG, La Plaine Saint Denis (FR)

(72) Inventors: Audrey Le Gouellec, Uriage (FR); Bertrand Toussaint, Saint Egreve (FR); Jean-Luc Lenormand, Meylan (FR); David Laurin, Grenoble (FR); Elodie Meynet, La Tronche (FR)

(73) Assignees: Universite Grenoble Alpes, Saint Martin d'Heres (FR); Centre Hospitalier Universitaire Grenoble Alpes, La Tranche (FR); Establissement Francais Du Sang, Saint Denis (FR)

( * ) Notice: Subject to any disclaimer, the term of this patent is extended or adjusted under 35 U.S.C. 154(b) by 0 days.

(21) Appl. No.: 16/486,410

(22) PCT Filed: Feb. 15, 2018

(86) PCT No.: PCT/EP2018/053744
§ 371 (c)(1),
(2) Date: Aug. 15, 2019

(87) PCT Pub. No.: WO2018/149904
PCT Pub. Date: Aug. 23, 2018

(65) Prior Publication Data
US 2020/0023052 A1 Jan. 23, 2020

(30) Foreign Application Priority Data
Feb. 16, 2017 (EP) .................... 17305173

(51) Int. Cl.
A61K 39/104 (2006.01)
A61P 31/04 (2006.01)
A61K 39/00 (2006.01)

(52) U.S. Cl.
CPC ............ *A61K 39/104* (2013.01); *A61P 31/04* (2018.01); *A61K 2039/522* (2013.01); *A61K 2039/575* (2013.01)

(58) Field of Classification Search
None
See application file for complete search history.

(56) References Cited

U.S. PATENT DOCUMENTS 7,939,319 B2    5/2011  Polack et al.
9,556,442 B2    1/2017  Le Gouellec et al.
2008/0187520 A1  8/2008  Polack et al.
2014/0335125 A1 11/2014  Le Gouellec et al.
2017/0114319 A1  4/2017  Le Gouellec et al.
2018/0078746 A1  3/2018  Cinquin et al.

FOREIGN PATENT DOCUMENTS

WO    WO-2013/087667 A1    6/2013

OTHER PUBLICATIONS

Epaulard, O., et al.; "Optimization of a type III secretion system-based *Pseudomonas aeruginosa* live vector for antigen delivery;" Clinical and Vaccine Immunol., vol. 15, No. 2, Feb. 2008; pp. 308-313.
Brockstedt, D. G., et al.; "Killed but metabolically active microbes: a new vaccine paradigm for eliciting effector T-cell responses and protective immunity;" Nat. Med., vol. 11, No. 8, Aug. 2005; pp. 853-860.
Epaulard, O. T., et al.; "Anti-tumor immunotherapy via antigen delivery from a live attenuated genetically engineered *Pseudomonas aeruginosa* type III secretion system-based vector;" Mol. Ther., vol. 14, No. 5, Nov. 2006; pp. 656-661.
Wollowitz, S.; "Fundamentals of the psoralen-based Helinx technology for inactivation of infectious pathogens and leukocytes in platelets and plasma;" Seminars in Hematol., vol. 38, No. 4, Supp. 11, Oct. 2001; pp. 4-11.
DeBell, R. M.; "Production of exotoxin A by *Pseudomonas aeruginosa* in a chemically defined medium;" Infection and Immun., vol. 24, No. 1, Apr. 1979; pp. 132-138.
Buonaguro, L., et al.; "Translating tumor antigens into cancer vaccines;" Clinical and Vaccine Immunol., Minreview, vol. 18, No. 1, Jan. 2011; pp. 23-34.
Novellino, L., et al.; "A listing of human tumor antigens recognized by T cells: Mar. 2004 update;" Cancer Immunol Immunother, 54(3), Mar. 2005; pp. 187-207.
Derouazi, M., et al.; "Optimal epitope composition after antigen screening using a live bacterial delivery vector: application to TRP-2;" Bioeng. Bugs, 1 (1), Jan.-Feb. 2010; pp. 51-60.
Dacheux, D., et al.; "Cell death of human polymorphonuclear neutrophils induced by a *Pseudomonas aeruginosa* cystic fibrosis isolate requires a functional type III secretion system;" Infection and Immun., vol. 67, No. 11, Nov. 1999; pp. 6164-6167.
Papezova, K., et al.; "Ordered expression of virulence genes in *Salmonella enterica* serovar typhimurium;" Folia Microbiologica, Praque, CZ, vol. 52, No. 2, Jan. 1, 2007, XP002587756; pp. 107-114.
Harcombe, W. R., et al.; "Impact of phages on two-species bacterial communities;" Applied and Environmental Microbiology, vol. 71, No. 9, Sep. 2005, XP002676592; pp. 5254-5259.

(Continued)

*Primary Examiner* — Jennifer E Graser
(74) *Attorney, Agent, or Firm* — Harness, Dickey & Pierce, PLC

(57) ABSTRACT

The present disclosure is related to a live-attenuated strain of *Pseudomonas* for its use as a vaccine, and for use in a method for preventive immunizing and for treating *Pseudomonas* infection, in particular in patients suffering from cystic fibrosis. Preferably, the live-attenuated strain of *Pseudomonas* is furthermore treated to become 'killed but metabolically active'.

9 Claims, 8 Drawing Sheets

(56) References Cited

OTHER PUBLICATIONS

Martin, C. H., et al.; "High-titer production of monomeric hydroxyvalerates from levulinic acid in *Pseudomonas putida*;" Journal of Biotechnology, Elsevier Science Publishers, Amsterdam, NL, vol. 139, No. 1, Jan. 1, 2009, XP025796274; pp. 61-67.

Chan, R., et al.; "Influence of culture conditions on expression of the mucoid mode of growth of *Pseudomonas-aeruginosa*;" Journal of Clinical Microbiology, vol. 19, No. 1, Jan. 1984, XP002676593; pp. 8-16.

Blumentals, I. I., et al.; "Development of a defined medium and two-step culturing method for improved exotoxin a yields from Pseudomonas-aeruginosa", Applied and Environmental Microbiology, vol. 53, No. 9, Sep. 1987, XP002676594; pp. 2013-2020.

Lankowski, A. J., et al.; "Killed but metabolically active *Salmonella typhimurium*: application of a newtechology to an old vector;" Journal of Infectious Diseases, University of Chicago Press, Chicago, Illinois, vol. 195, No. 8, Apr. 1, 2002, XP009099076; pp. 1203-1211.

Skoberne, M., et al.; "KBMA *Listeria monocytogenes* is an effective vector for DC-mediated induction of antitumor immunity;" Journal of Clinical Investigation, vol. 118, No. 12, Dec. 2008, XP002676595; 12 pages.

Skoble, J., et al.; "Killed but Metabolically Active *Bacillus anthracis* Vaccines Induce Broad and Protective Immunity against Anthrax," Infection and Immunity, vol. 77, No. 4, Apr. 2009, XP002676596; pp. 1649-1663.

Wang, Y., et al.; "Optimization of Antitumor Immunotherapy Mediated by Type III Secretion System-Based Live Attenuated Bacterial Vectors," Journal of Immunotherapy, vol. 35, No. 3, Apr. 1, 2012, XP009159387; pp. 223-234.

Le Gouëllec, A. et al., "A Safe Bacterial Microsyringe for In Vivo Antigen Delivery and Immunotherapy," Molecular Therapy, vol. 21, No. 5, May 1, 2013, 11 pages.

Priebe, G. P., et al., "IL-17 is a Critical Component of Vaccine-Induced Protection against Lung Infection by Lipopolysaccharide-Heterologous Strains of *Pseudomonas aeruginosa*," The Journal of Immunology, vol. 181, No. 7, Oct. 1, 2008.

Dubensky, T. W., et al., "Killed but metabolically active vaccines," Current Opinion in Biotechnology, vol. 23, No. 6, Dec. 1, 2012.

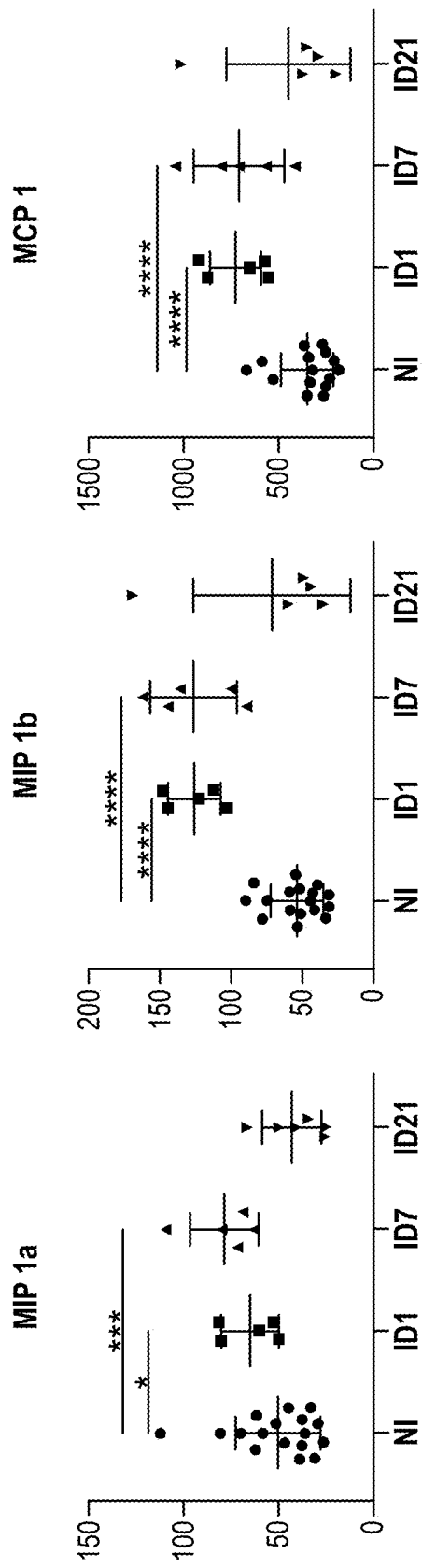

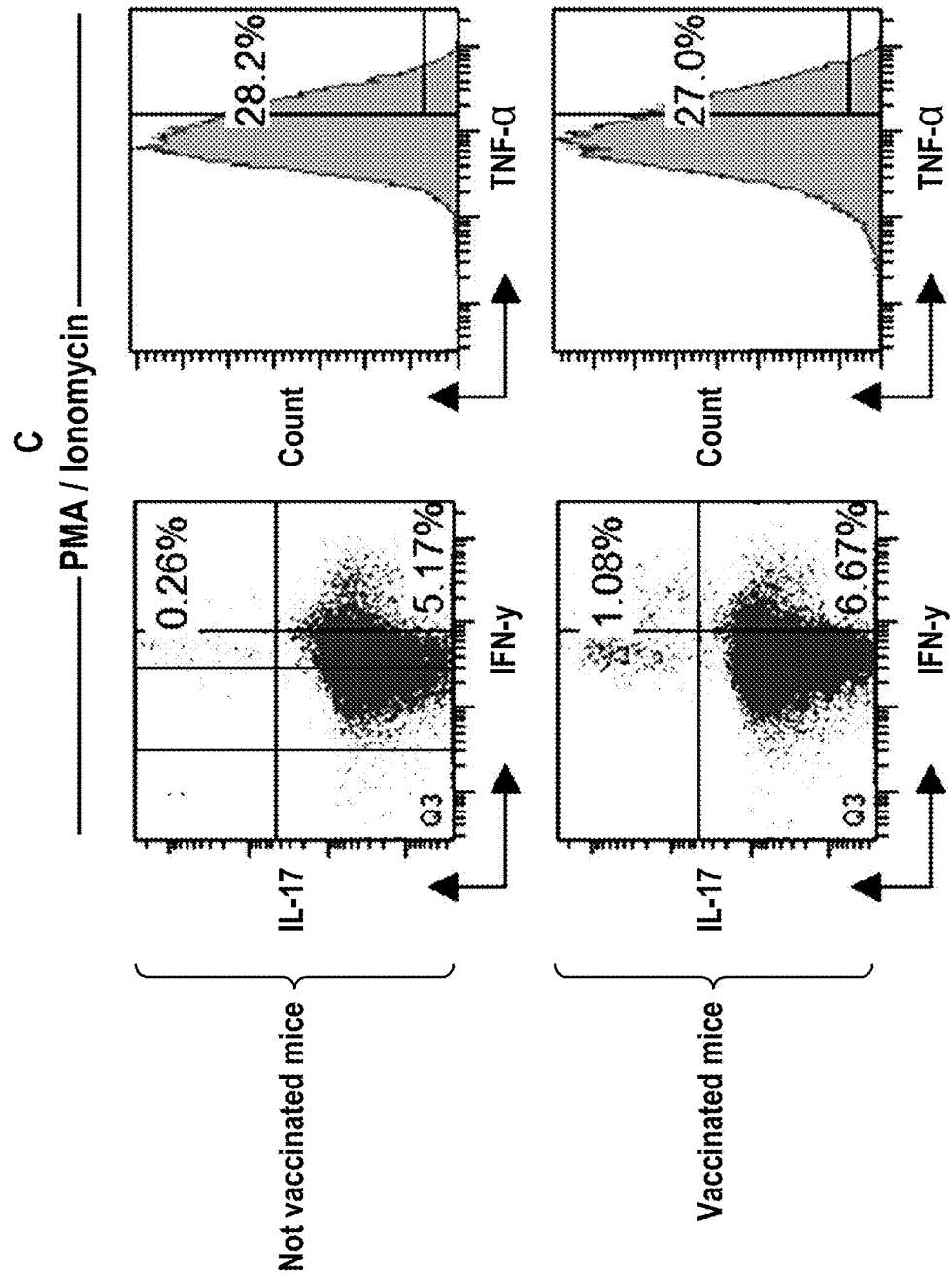

ATTENUATED STRAIN OF PSEUDOMONAS AS A VACCINE FOR PSEUDOMONAS INFECTION

CROSS-REFERENCE TO RELATED APPLICATIONS

This application is a National Phase Entry of International Patent Application No. PCT/EP2018/053744, filed on Feb. 15, 2018, which claims priority to European Patent Application Serial No. 17305173.1, filed on Feb. 16, 2017, both of which are incorporated by reference herein.

TECHNICAL FIELD

The present invention concerns the medical field and in particular vaccination field. Specifically, the present invention is related to a live-attenuated strain of *Pseudomonas* for its use as a vaccine, and for use in a method for preventive immunizing and for treating *Pseudomonas* infection, in particular in patients suffering from cystic fibrosis.

BACKGROUND

*Pseudomonas aeruginosa* is purveyor of an important morbidity and mortality especially in cystic fibrosis patients, and its eradication is difficult because of a huge phenotypic adaptability and thus an increase in resistance to antibiotics. Cystic fibrosis (CF) is an inherited disease due to a defect in the CFTR gene encoding a membranous chloride channel. In the lungs of CF patients, primary defenses against bacteria are disturbed and patients rapidly suffer from infections with different bacteria. *Pseudomonas aeruginosa* (*P. aeruginosa*) is by far the most significant pathogen in CF adults and, it appears that pulmonary infections with this pathogen occur much earlier than believed previously in children (1-4). *P. aeruginosa* is a bacterium with a large genome particularly well adapted to colonize lungs of CF patients, firstly via the expression of molecular factors in response to host defenses (5-9), and secondly by its capacity to develop antimicrobial resistance mechanisms. The average prevalence of *P. aeruginosa* infections in these patients is 57.8% and increases with age (4), and the acquisition of this microorganism is associated with a clinical poor outcome (6-9).

Curative treatments such as antibiotics are not sufficient to eradicate *P. aeruginosa*. Indeed, this microorganism is particularly resistant to the current antibiotic arsenal; it displays intrinsic multidrug resistance and has a tremendous capacity to acquire further resistance mechanisms (10, 11). Moreover, during chronic infections this organism can sometimes adopt a mucoid phenotype and is also thought to adopt a biofilm-like mode of growth, resulting in protection from host immune system and antibiotic attack, with oxygen limitation and low bacterial metabolic activity (12). Thereby, the best would be to develop a vaccination strategy, as curative but also prophylactic therapy, that would limit chronic colonization of CF lungs by *P. aeruginosa* and by this way acute pulmonary infection, and maintain an optimal composition of pulmonary microbiota. But after 40 years of research and clinical trials up to phase 3, no biotechnology company has met the challenge of achieving a safe, immunogenic and effective vaccine.

Some literatures reviewed several studies conducted to date and attempted to dissect the necessary elements for a good immunization coverage against *P. aeruginosa* (13-15). It appears that only a vaccine which would cause a broad immune response (humoral and cellular) would be protective and could help to neutralize or eliminate this microorganism.

A number of recombinant vaccines have already been tested and some elements stand out as important to elicit a good immune response. Those are lipopolysaccharide (LPS), alginate, flagellum, type 3 secretion system (T3SS) with PopB and PcrV, and outer membrane proteins OprF and OprI. But these recombinant vaccines, despite numerous clinical trials, failed to be protective for CF patients probably due to the phenotypic plasticity of *P. aeruginosa*. However, a recent Cochrane Database (16) comparing several trials on *P. aeruginosa* vaccines to placebo or no intervention concluded that vaccines against *P. aeruginosa* cannot currently be recommended in patients with CF.

After the failure of several recombinant vaccines which solicit only humoral response, live-attenuated vaccines are the focus of attention as they elicit a broad immune response (humoral and cellular) indispensable to fight against its pathogen (17). For example, *P. aeruginosa* mutants having a deletion of the aroA gene, which is required for the synthesis of aromatic amino acids, have proven to be both highly attenuated and immunogenic in animal models (18, 19). These live-attenuated *P. aeruginosa* vaccine strains confer a T cell-mediated immune response which protect rodents during infectious challenge, regardless the associated LPS serotype and the production of neutralizing antibodies (22,23). Indeed, IL-17 cytokine produced in large amounts by the T cells is found in great quantity in the bronchoalveolar lavage and participated in the massive recruitment of neutrophils in the airways and thus in the antibacterial response (20). Moreover, the depletion of IL-17 before the challenge of the immunized mice or the absence of IL-17 receptor (IL-17R) proves that IL-17, and therefore the cellular immune response (Th17 pathway), is necessary to obtain a good protection of the vaccine in a mouse model (20). Several studies have shown an important role of IL-17 in innate and adaptive antibacterial defenses, particularly during *Klebsiella pneumoniae* (21,22), *Bacteroides fragilis* (23) and *Escherichia coli* (24) lung infections. Some proteins have been identified in *P. aeruginosa* to cause a high secretion of IL-17 such as PopB, FpvA, FptA, OprL and PilIQ (25). The purified PopB protein which belongs to the translocon of the T3SS (highly conserved element) generates a strong Th17 response which contributes to the increasing clearance of *P. aeruginosa* in lung and spleen after challenge (25). All these data suggest the interest to explore the development of a vaccine candidate which involves multiple immune effectors, and not only opsonic antibodies production against LPS O antigen or other antigens of the bacterium.

For the *P. aeruginosa*-based vaccine, type III secretion system (T3SS) has been demonstrated by many laboratories to be a major virulence factor of this bacterium. The T3SS apparatus is like an injectisome dedicated to the injection of toxins inside host cells (29). Recently, it has been shown that this injectisome could be hijack to inject proteins of interest, and this could help in the development of a novel antigen delivery tool (30).

In 2013, Le Gouëllec et al. have applied the KBMA attenuation strategy on *P. aeruginosa* to develop a microsyringe for antigen delivery based on the T3SS of this bacterium (30). They have shown that the KBMA has the potential to deliver antigens to human antigen-presenting cells in vitro via T3SS with considerable attenuated cytotoxicity as compared with the wild-type vector (31). In a mouse model of cancer, this KBMA strain which cannot replicate in its host, efficiently disseminates into lymphoid organs and delivers its heterologous antigens (31). The attenuated strain effectively induces a cellular immune response against the cancerous cells while lowering the systemic inflammatory response.

The inventors have now surprisingly shown that the use of a live-attenuated *Pseudomonas* strain is able to elicit a safe, immunogenic and effective response against *Pseudomonas* infection. Therefore, they showed that the live-attenuated *Pseudomonas* strain developed in the prior art as a vehicle or tool for delivering a specific protein of interest, and in particular tumoral antigens, is an efficient vaccine against *Pseudomonas* infection when used as an empty vehicle, viz. with no specific protein of interest to be delivered. Furthermore, they demonstrated the ability to rationally design this vaccine against *Pseudomonas* infection by overexpression of beneficial effectors in order to obtain the broadest immune response as possible and/or by modification to improve safety of such a vaccine based on killed but metabolically active attenuation method. The present invention thus provides an innovative and safer live-attenuated *Pseudomonas* vaccine.

SUMMARY

The present invention is related to a live-attenuated strain of *Pseudomonas* for use in a method for preventive immunizing a patient prone to suffer from a *Pseudomonas* infection or for treating a patient suffering from a *Pseudomonas* infection, said live-attenuated strain comprising deletion of the genes ExoS, ExoT. Preferably, this live-attenuated strain of *Pseudomonas* for use in a method for preventive immunizing a patient prone to suffer from a *Pseudomonas* infection or for treating a patient suffering from a *Pseudomonas* infection, further expresses the gene ExsA encoding the activator of the *Pseudomonas aeruginosa* type III secretion system, and the sequence encoding the 54 first amino acids of the ExoS toxin (exoS54). In an advantageous embodiment of the invention, the live-attenuated *Pseudomonas* strain to be used according to the invention is furthermore treated with the KBMA process to become 'killed but metabolically active'.

In a preferred embodiment, the live-attenuated *Pseudomonas* strain to be used according to the invention may further express beneficial effectors so as to obtain the broadest immune response as possible, and in particular express at least one of the following proteins: proteins of the main virulence factor T3SS, such as PopB, PopD, PscJ, PscI and PcrV; proteins of the flagella, such as FliC; and porin such as OprF and OprI. The invention is also related to a vaccine comprising at least the live-attenuated strain of *Pseudomonas* as defined above and a pharmaceutically acceptable carrier or adjuvant. The present invention is also related to a vaccination strategy characterized by multi-position injections of the live-attenuated strain of *Pseudomonas*, to the organism. In particular, the present invention is thus related to a method of inducing an immune response in a patient prone to suffer from a *Pseudomonas* infection or in a patient suffering from a *Pseudomonas* infection, comprising administering to said patient by injection in multiple positions an effective amount of the above-described vaccine. Finally, the invention is also related to the use of the live-attenuated strain of *Pseudomonas* as defined above for preparing a vaccine.

DETAILED DESCRIPTION

Figure 1A:
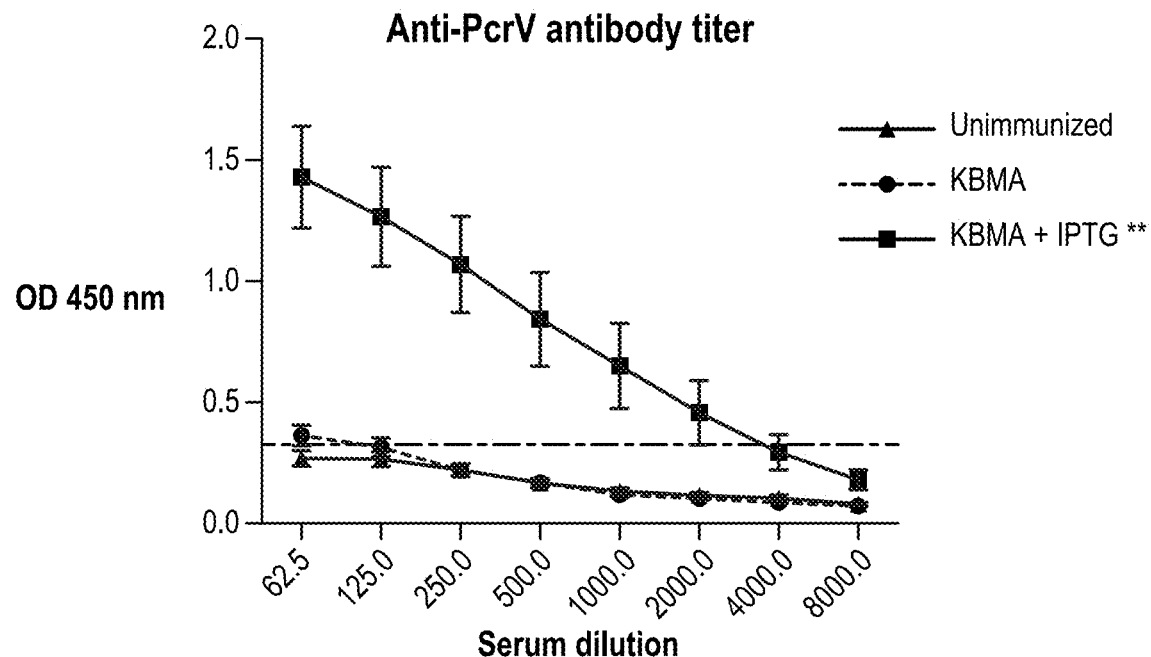
FIGS. 1A and 1B are graphs showing polyvalent humoral responses elicited by a vaccine vector KMBA.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Sambrook et al., 2001. Conventional immunological techniques are explained in Current protocol in Immunology, Coligan, John Wiley & Sons (2005).

It must be noted that as used herein and in the appended claims, the singular forms "a", "an", and "the" include plural reference unless the context clearly dictates otherwise. Thus, for example, a reference to "a strain" includes a plurality of such strains, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

As used herein, the following terms may be used for interpretation of the claims and specification. In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "*Pseudomonas*" designates a genus of gammaproteobacteria belonging to the family Pseudomonadaceae containing 191 validly described species. Ali species and strains of *Pseudomonas* are Gram-negative rods, and are classified as strict aerobes. Among them, *Pseudomonas aeruginosa* is a highly relevant opportunistic human pathogen. Gram-negative bacteria use different types of secretion systems for their own purposes. In particular, the type III secretion system (T3SS) is involved in the cytotoxicity of *Pseudomonas* strains.

The present invention is related to a live-attenuated strain of *Pseudomonas* for use in a method for preventive immunizing a patient prone to suffer from a *Pseudomonas* infection or for treating a patient suffering from a *Pseudomonas* infection, wherein said live-attenuated strain comprising deletion of the genes ExoS, ExoT. Advantageously, the live-attenuated strain of *Pseudomonas* for use in a method for preventive immunizing a patient prone to suffer from a Pseudomonas infection or for treating a patient suffering from a Pseudomonas infection further expresses the gene ExsA encoding the activator of the Pseudomonas aeruginosa type III secretion system and the sequence encoding the 54 first amino acids of the ExoS toxin (exoS54). In one embodiment, the live-attenuated strain of Pseudomonas to be used as described above, comprises deletion of the genes ExoS, ExoT, expresses the gene ExsA encoding the activator of the Pseudomonas aeruginosa type III secretion system and the sequence encoding the 54 first amino acids of the ExoS toxin (exoS54), and further expresses Orf1 (also named SpcS) the specific chaperone of ExoS.

Indeed, the inventors demonstrated that a specific live-attenuated Pseudomonas, and in particular a specific live-attenuated Pseudomonas aeruginosa "killed but metabolically active", elicited a high and broad humoral immune response in mice against several antigens of particular interest such as OprF porin and PcrV protein, a component of the type 3 secretion system, the major virulence factor of Pseudomonas aeruginosa. They also demonstrated that while stimulating humoral immunity, this specific live-attenuated Pseudomonas aeruginosa elicited also several pathways of cellular immunity, especially Th1, Th2 and especially Th17, known as necessary to eradicate this bacterium. Moreover, they demonstrated that the vaccine strain according to the present invention is safe and has a protective efficacy in mice during a pulmonary infectious challenge.

The live-attenuated Pseudomonas strain to be used according to the present invention comprises at least deletion of the genes encoding the two major T3S toxin exoenzymes—ExoS and ExoT. In particular, such a live-attenuated Pseudomonas strain may be obtained starting from the initial strain CHA (wild-type, P. aeruginosa mucoid strain as described in (Toussaint, B., I. Delic-Attree and P. M. Vignais (1993). "Pseudomonasaeruginosa contains an IHF-like protein that binds to the algD promoter." Biochem Biophys Res Commun 196(1): 416-421). Advantageously the live-attenuated Pseudomonas strain to be used according to the invention is a strain which is already attenuated by deletion of these two genes such as CHA-OST as described by Epaulard O, Derouazi M, Margerit C, Marlu R, Filopon D, Polack B, et al. Optimization of a type III secretion system-based Pseudomonas aeruginosa live vector for antigen delivery. Clin Vaccine Immunol 2008 February; 15(2):308-13.

For the aspect of the present invention where the live-attenuated Pseudomonas strain further exhibit other features with relation to ExsA and the sequence encoding the 54 first amino acids of the ExoS toxin (exoS54), optionally with expression of Orf1 (SpcS) the chaperone protein of ExoS, a strain which is already attenuated by deletion of the two genes ExoS and ExoT such as CHA-OST as described by Epaulard et al. 2008 (supra) may be modified to expression those other features, and in particular transformed with a plasmid containing all the other necessary sequences as defined above, as for example with the plasmid pEiS54 (GeneBankJQ733380, version 1 of Mar. 14, 2012) for exhibiting the other requested features. Whatever the aspect of the invention, the live-attenuated strain of Pseudomonas to be used is advantageously furthermore treated to become 'killed but metabolically active'.

The process to obtain a "killed but metabolically active" bacteria can be summarized as follow:
    deleting the gene uvrAB encoding exonucleotidase A and B subunit; any technique known by the man skilled in the art can be used to obtain this deletion; and A photochemical inactivation with UVA is performed in presence of psoralen.

Toxicity and optionally secretion via the TTSS system by the thus treated strain may be assessed. For more details on the KBMA process, see Brockstedt et al., 2005 (Brockstedt D G, Bahjat K S, Giedlin M A, Liu W, Leong M, Luckett W, Gao Y, Schnupf P, Kapadia D, Castro G, Lim J Y, Sampson-Johannes A, Herskovits A A, Stassinopoulos A, Bouwer H G, Hearst J E, Portnoy D A, Cook D N, Dubensky T W Jr. Killed but metabolically active microbes: a new vaccine paradigm for eliciting effector T-cell responses and protective immunity. Nat Med. 2005 August; 11(8):853-60) and Wollowitz, 2001 (Wollowitz S. Fundamentals of the psoralen-based Helinx technology for inactivation of infectious pathogens and leukocytes in platelets and plasma. Semin Hematol. 2001 October; 38(4 Suppl 11):4-11), herein incorporated by reference.

In a preferred embodiment of the invention, a KBMA live-attenuated strain of Pseudomonas may be obtained by culturing the live-attenuated strain of Pseudomonas with deletion of the gene uvrAB encoding exonucleotidase A and B subunit and exposure to long wavelength UVA light in presence of psoralen. Preferably, the exposure is carried out in presence of a concentration of 10 µM psoralen during 40 minutes prior to exposition to UVA irradiation at a dose of 7.2 J/cm² (about 365 nm) during 40 minutes. In addition, the inventors demonstrated that the live-attenuated strain of Pseudomonas to be used according to the invention is an engineered life biological product which may be rationally designed by overexpressing beneficial effectors for optimization of the vaccination efficacy in order to obtain the broadest immune response as possible. In an advantageous embodiment of the present invention, the live-attenuated strain of Pseudomonas to be used is further expressing at least one of the following proteins: proteins of the main virulence factor T3SS, such as PopB, PopD, PscJ, PscI and PcrV; proteins of the flagella, such as FliC; and porin such as OprF and OprI.

Also, as described above, a Pseudomonas strain which is already attenuated by deletion of the aroA gene encoding the 3-phosphoshikimate 1-carboxyvinyltransferase which is a key enzyme in aromatic amino acid synthesis and/or of the lasI gene encoding the enzyme which produces quorum sensing (QS) homoserine lactones 3-oxo-C12-HSL may be used as starting strain for obtaining the live-attenuated strains to be used according to the invention. As previous described, Pseudomonas strains with attenuation of its virulence while keeping a good efficiency to induce an immunogenic response when administered to an organism, are already available in the art, such as for example CHA-OST and CHA-OAL (Epaulard et al., 2008 supra). In a preferred embodiment of the invention, the live-attenuated Pseudomonas strain belongs to the species Pseudomonas aeruginosa. In another preferred embodiment, the present invention is related to the live-attenuated strain of Pseudomonas for use as defined above in a method for preventive immunizing or for treating a patient suffering from cystic fibrosis, since these patients are particularly disposed to pathogens and especially to Pseudomonas infection.

The invention is also related to a vaccine comprising at least the live-attenuated strain of Pseudomonas such as described above and a pharmaceutically acceptable carrier or adjuvant. The man skilled in the art knows the best adjuvant for each vaccine composition. The present invention is also related to a method of inducing an immune response in a host comprising administering to the host by injections in multiple positions an effective amount of the vaccine such as described above, and preferably said host is a patient prone to suffer from a *Pseudomonas* infection or in a patient suffering from a *Pseudomonas* infection. Finally, the invention is also related to the use of the live-attenuated strain of *Pseudomonas* such as described above, for preparing a vaccine composition.

FIG. 1: Polyvalent humoral response elicited by the vaccine vector KBMA. ELISAs were performed on sera of immunized with either KBMA (n=6) or KBMA+IPTG (n=18) and unimmunized mice (n=18) collected 3 weeks after the last immunization. A) PcrV and B) OprF as coated antigens. Non-parametric unpaired Mann-Whitney t tests were used for statistical analysis. Error bars are SEM. Positive threshold of 0.26 for PcrV and 0.51 for OprF. *$p<0.005$, ****$p<0.0001$. OD: optical density.

Figure 2:
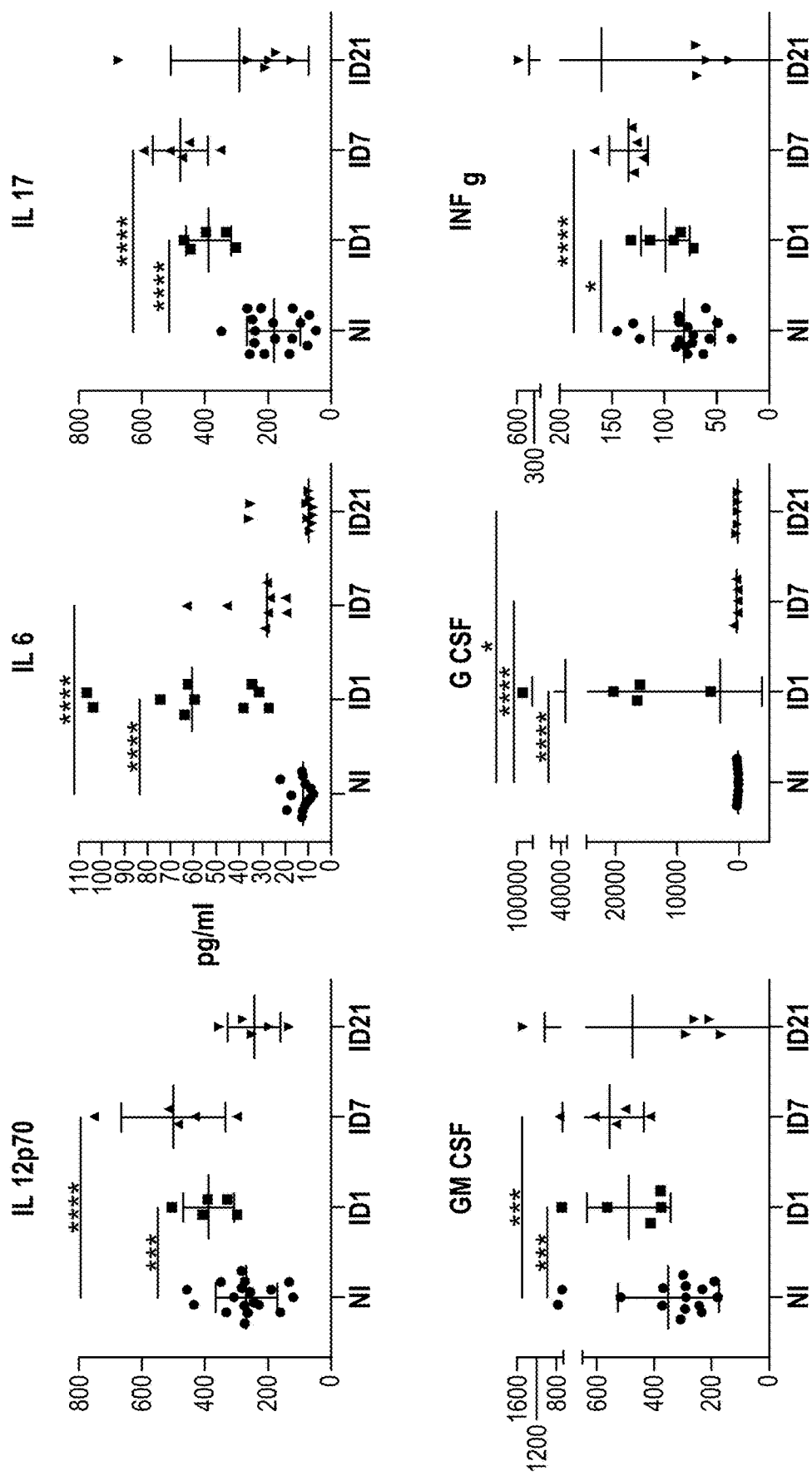
FIG. 2 is a set of graphs showing cellular responses elicited by the vaccine vector KMBA.
Figure 2:
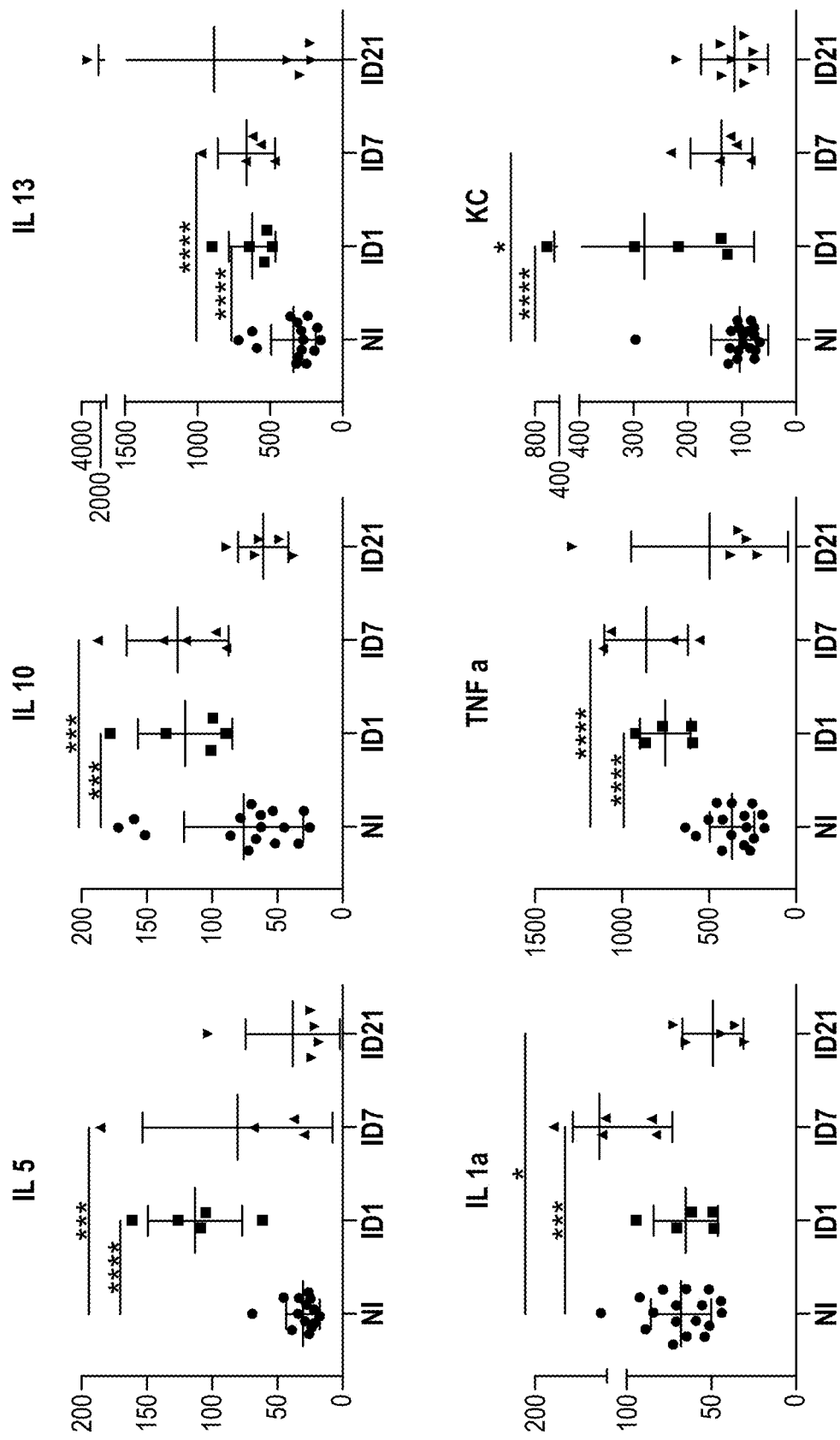

FIG. 2: Cellular response elicited by the vaccine vector KBMA. A multiplex immunoassay was performed in duplicate to determine the expression levels of 23 different cytokines in sera samples of immunized (n=10 per group) and unimmunized mice (n=30: pool of all unimmunized mice) collected at days 1, 7 and 21 after the last immunization. Only the cytokines that were significantly different from the control (*$p<0.05$) are shown in mice immunized with KBMA+IPTG. Non-parametric unpaired Mann-Whitney t tests were used for statistical analysis. Scatter plots represent averages and bars mean with SD. *$p<0.05$, $p<0.005$, *$p<0.0005$, ****$p<0.0001$. D1: day 1; D7: day 7; D21: day 21 after the last immunization.

Figure 3:
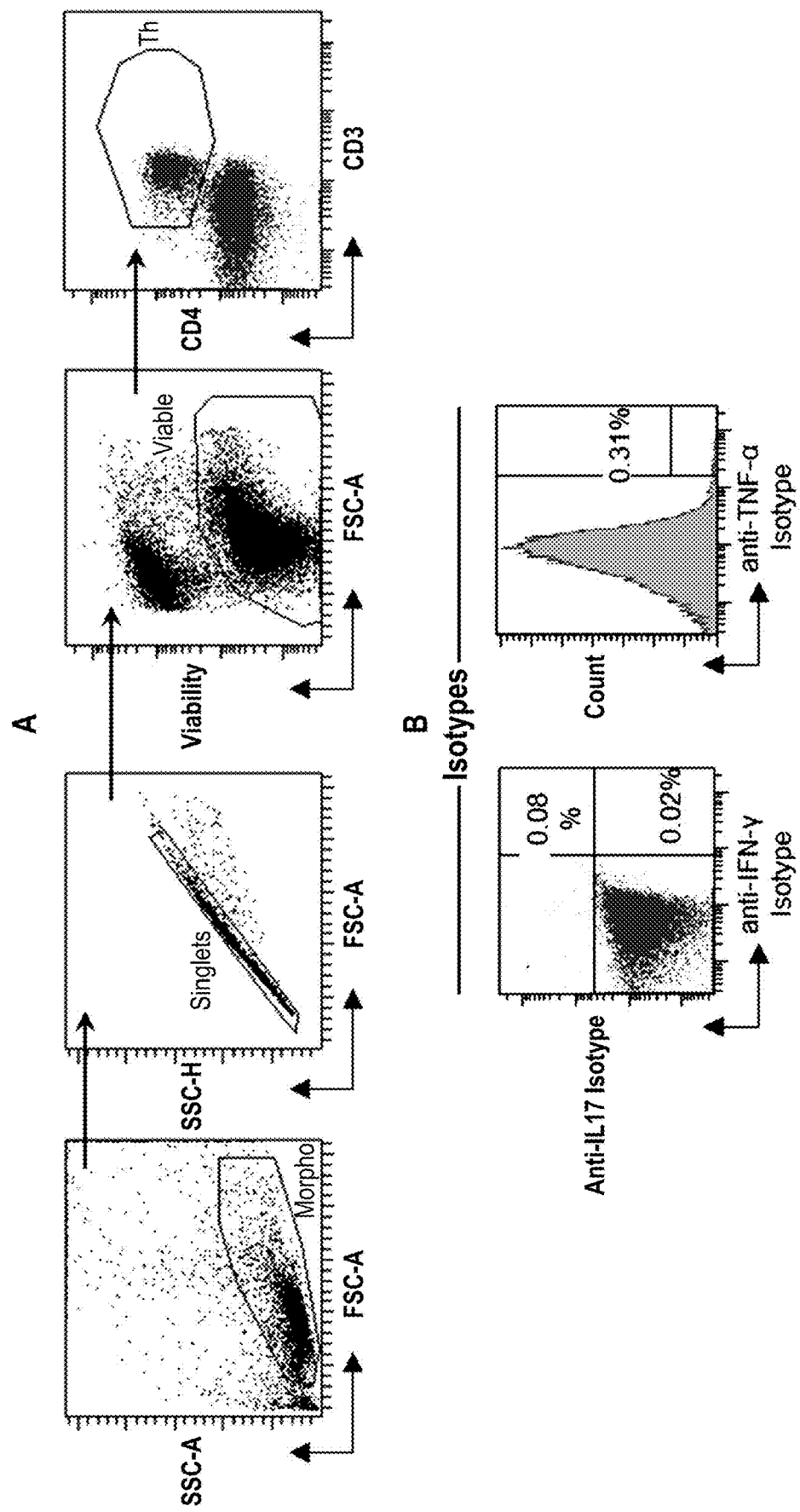
FIG. 3 is a set of graphs showing cellular responses elicited by the vaccine vector KMBA.
Figure 3:
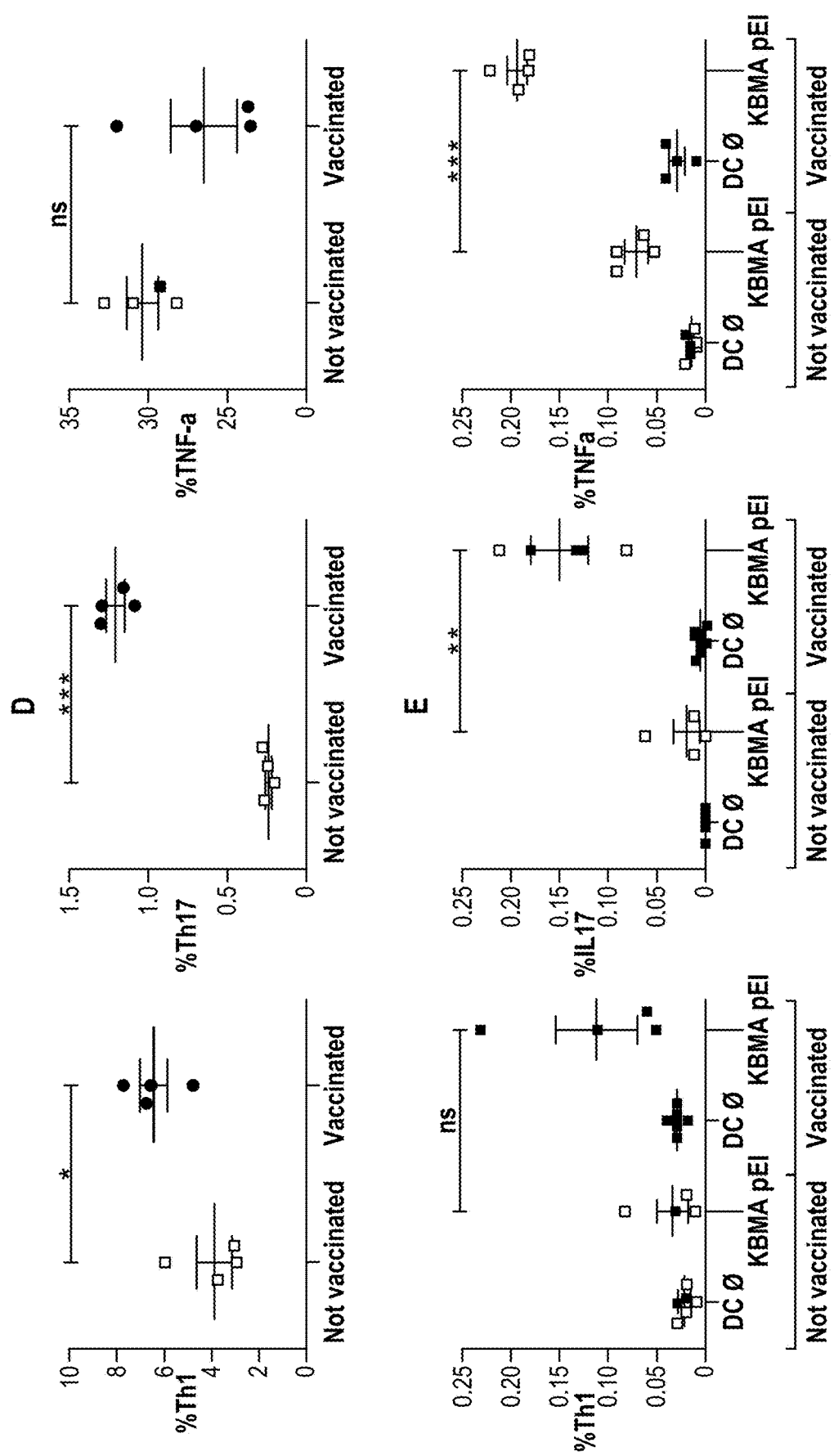

FIG. 3. Cellular response elicited by the vaccine vector KBMA. A) Flow cytometry successive gating strategy for detection of helper T cells from the spleen. The singlets cells without damaged membranes and thus not permeable to the reactive dye were considered as viable cells and gated on $CD3^+CD4^+$. B) Flow cytometry threshold strategy for detection of helper T cells effector activity by cytokine intracellular staining assay. Isotypes control antibodies were used to set-up the background. C and D) Unspecific stimulations with PMA/iono were used to analyze the frequency of helper T cells producing IL-17 defining the Th17 subtype and IFN-γ but not the IL-17 defining the Th1. We also analyzed the TNF-α production by the helper T cells. C) Shows a single example of helper T cells cytokine production by spleen cells from unimmunized mice and immunized mice. D) Summarize the data. E) Syngeneic $DC_{2.4}$ APCs presenting KBMA antigens (KBMA) after overnight processing were used to stimulate spleen and measure the helper T cells specific responses to the KBMA vaccine. APCs not exposed to the bacteria (DC Ø) were used as negative stimulating condition for background evaluation. D and E) Mean and SEM frequency of Th17, Th1 and TNF-α helper T cells is depicted for unimmunized mice and immunized mice. Unpaired t test differences between the two groups are indicated (*$p<0.05$, $p<0.005$, *$p<0.0005$).

Figure 4:
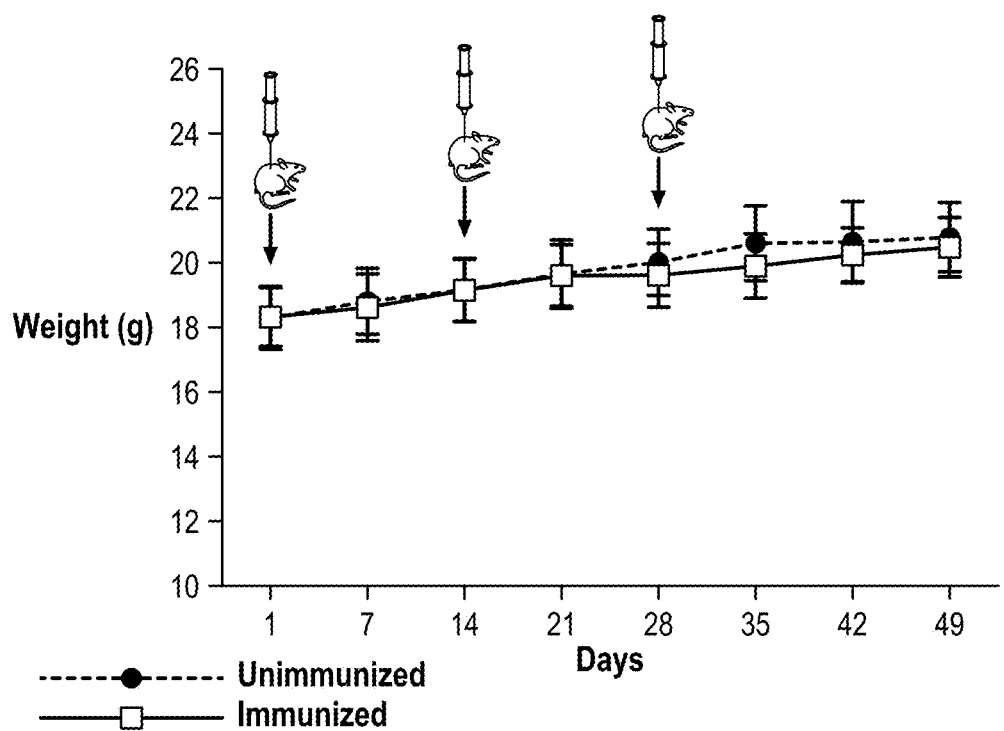
FIG. 4 is a graph showing no toxicity on weight for the vaccine vector KMBA.

FIG. 4. No toxicity on weight for the vaccine vector KBMA. Immunized (n=35) and unimmunized mice (n=30) were weighted weekly since the first immunization to the intranasal infectious challenge. Non parametric unpaired Mann-Whitney t test was used for statistical analysis. Error bars are mean with SD, p=0.4418.

Figure 5:
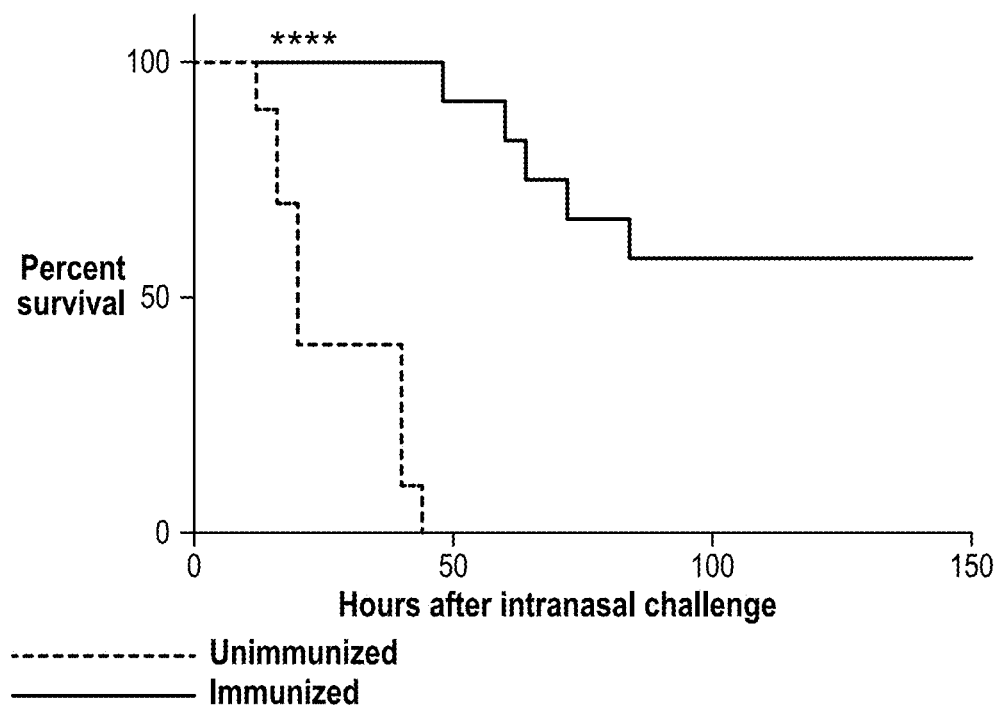
FIG. 5 is a graph showing protective efficacy conferred by the vaccine vector KMBA.

FIG. 5. Protective efficacy conferred by the vaccine vector KBMA. Intranasal infectious challenge with $5 \times 10^6$ CFU/mouse of CHA strain were performed on KBMA+IPTG immunized mice (n=12) and unimmunized mice (n=10), 3 weeks after the last immunization. Animals were then observed for survival every four hours for up to one week, animal health was recorded and mice were euthanized if necessary according to different clinical signs. Log-rank test was used for statistical analysis. ****$p<0.0001$.

EXAMPLES

Before describing the present invention in detail, it is to be understood that this invention is not limited to particularly exemplified methods and may, of course, vary.

Bacterial Strains, Plasmids and Media

The bacterial strains and plasmids used in this work are listed in Table 1.

TABLE 1

| Name | Relevant features |
|---|---|
| Bacterial strains | |
| CHA | Wild type, *P. aeruginosa* mucoid strain, CF isolate from CHU Grenoble |
| OST | CHA strain deleted for Exotoxins S and T (ΔexoS, ΔexoT) |
| OSTAB2 | CHA-OST strain deleted for uvrA and uvrB genes (ΔuvrA::loxΔuvrB::lox), susceptible to photochemical treatment |
| OSTAB2 pEiS54 | CHA-OSTAB2 transformed with empty plasmid pEAi-S54 (inducible exsA gene; secretion tag) |
| Plasmids | |
| pEiS54 | Empty plasmid with inducible exsA gene and secretion tag |
| pET15b-pcrV | Gift from Ina Atree (CEA, Grenoble, France) |

The photochemical sensitive strain OSTAB2 mutant was previously generated from the *P. aeruginosa* strain CHA-OST (35) by deleting uvrA and uvrB genes by Cre/lox-based mutagenesis (36). The strain is transformed with pEiS54 plasmid (GenBank accession number JQ733380, version 1 of Mar. 14, 2012). Media used for bacterial cultures were Lysogeny broth (Miller) and *Pseudomonas* isolation agar (PIA, Difco™, BD). Medium used for cell cultures was Iscove's Modified Dulbecco's Media (IMDM, Sigma-Aldrich). Whenever it is cited, carbenicillin (Cb) concentration was used at 300 µg/ml, isopropyl-beta-D-thiogalactopyranoside (IPTG) at 0.5 mM and gentamicin at 50 µg/ml (Sigma-Aldrich).

Preparation of Vaccinal Strain

Frozen bacterial stocks of OSTAB2 pEiS54 strain were grown overnight in Lysogeny broth (LB) containing Cb, at 37° C., 300 rpm. After washing the overnight culture twice with 1 ml LB, bacteria were resuspended in culture at an optical density at 600 nm (OD600) of 0.2 in LB containing either Cb (condition KBMA) or Cb+IPTG (condition KBMA+IPTG) until the OD600 reached a value of 0.5. Inactivation of bacteria was then obtained using the photochemical treatment: after the addition of 10 µM of amotosalen (a gift from Grenoble EFS, France) in the culture medium and when the OD600 reached a value of 1, bacteria are subjected to illumination with UVA 365 nm (7.2 J/cm$^2$) during 40 minute, as previously described (31). Concentrations were adjusted spectrophotometrically and confirmed retrospectively by colony-forming units (CFU) counting on PIA at 37° C.

Immunization of Mice

We used female C57Bl/6J mice as they are known susceptible to chronic bronchopulmonary *P. aeruginosa* infection and able to produce high antibody levels and Th2 response (37,38). Mice were purchased at an age of 6-8 weeks from Janvier SA (Le Genest-Saint-Isle, France) and were kept under specific pathogen-free conditions in the PHTA animal facility at the University Grenoble Alpes (Grenoble, France). All mice were anesthetized (isoflurane) and inoculated three times by placing 100 µl of the vaccine preparation subcutaneously (SC) in the right flank with either KBMA or KBMA+IPTG. Escalating doses of $1\times10^8$ CFU/mouse, $2\times10^8$ CFU/mouse and $2\times10^8$ CFU/mouse were administered at fifteen days' interval.

Evaluation of the Humoral Immune Response

Anti-PcrV and anti-OprF specific antibodies were assessed by enzyme linked immunosorbent_assay (ELISA) using Nunc MaxiSorp® flat bottomed 96-well plates (Dutscher, France) coated overnight at 4° C. with 5 µg/mL of recombinant proteins as antigens in 0.01 M phosphate buffered saline (PBS), pH 7.4. For that, we have produced and purified the recombinant PcrV protein (from the clone BL21(DE3)pET15b-PcrV, a gift from Grenoble CEA, France); and the OprF porin in a proteoliposome (39). The plates were blocked with 2% BSA for 1 hour. Serial sera dilutions were added to each well and incubated for 1 hour. Following three washes with PBS containing 0.5% Tween 20, a peroxidase-conjugated sheep anti-mouse IgG (Sigma-Aldrich) diluted 1:1,000 in PBS was added and incubated for 1 hour. Then, 100 µL of 3,3',5,5'-tetramethylbenzidine (TMB) solution was added to each well, incubated for about 15 minutes in darkness, and then an equal volume of stopping solution (1N $H_2SO_4$) was added. Optical density at 450 nm was measured with a microplate reader (TriStar Berthold Technologies). For the interpretation of the results, a positive threshold corresponding to the upper limit of the negative controls was fixed (sum of the average of the negative controls plus three times the standard deviation).

Evaluation of the Cellular Immune Response

A multiplex immunoassay was used to determine the expression levels of 23 different cytokines in plasma samples (Bio-Plex Prom Mouse Cytokine Standard 23-Plex, Bio-Rad) of KBMA+IPTG immunized and unimmunized mice collected at days 1, 7 and 21 after the last immunization. The experiment was performed in duplicate according to the detailed instructions provided. Plate was read on Bio-Plex MAGPIX™ Multiplex Reader and analyzed with the software Luminex Xponent.

Thereafter, the spleen cells were harvested for ex vivo analysis and evaluated for effector activity by an intracellular staining assay using syngeneic $DC_{2.4}$ cell line (a gift from APcure, Grenoble) as professional antigen presenting cells (APCs) prepared using the procedure described hereinafter. The $DC_{2.4}$ APCs were exposed to KBMA during 1 hour, washed and then cultured for overnight antigen processing in RPMI1640 medium supplemented with antibiotics (50 µg/mL tobramycin and 200 µg/mL gentamicin) and 10% FCS. Then the APCs were counted and used to stimulate spleen cells at a ratio of 1 $DC_{2.4}$ to 10 spleen cells. APCs not exposed to the bacteria were used as control to measure the background responses by helper T cells. The spleen cells and targeted APCs were cocultured for 6 hours in the presence of 1 µg/mL brefeldin A protein transport inhibitor (BioLegend). Next, the cells were labeled with the Live/Dead FixableDead Cell Stain Kit (Invitrogen) and surface-labeled with antibodies specific for CD4 (RM4-5, BioLegend) and CD3 (145-2C11, BD Biosciences), and then labeled intracellularly with antibodies specific for mouse IFN-γ (XMG1 0.2), IL-17 (T TC11-18H10.1) and TNFα (MP6-XT22) (all from BioLegend) using cytofix/cytoperm and perm/wash reagents from BD Biosciences. Unspecific stimulation with 20 ng/mL phorbol 12-myristate 13-acetate (PMA)+1 µg/mL ionomycin (iono) were used to measure the total helper T cells producing $IL_{17}$ defining the Th17 subtype and IFN-γ but not the IL17 defining the $Th_1$ subtype and the TNF-α production. Samples were acquired on a FACSCanto II (BD Biosciences) and analyzed using Diva dedicated software.

Safety and Toxicity Assay

Immunized and unimmunized mice were weighed weekly since the day of the first vaccination until the challenge experiment to assess the impact of the vaccination on their growth. The vaccine preparation ready to use was frozen at −80° C. in LB+Cb+20% glycerol. In vitro cellular injection test was then performed to assess these storage conditions (40).

Efficacy Assay

Frozen bacterial stocks of CHA strain were grown overnight in LB without additional antibiotic, at 37° C., 300 rpm. After washing the overnight culture with 1 mL LB, bacteria were inoculated in LB at an OD600 of 0.2 and grown until an OD600 of 1.5-1.8 at 37° C., 300 rpm. Bacteria were resuspended in PBS. Concentrations were adjusted spectrophotometrically and confirmed after overnight growth on PIA at 37° C. An acute pulmonary infection was performed on mice by placing 20 µL of this bacterial suspension on each nostril (40 µl/mouse; $5\times10^6$ CFU/mouse) three weeks after the last immunization. Animals were then observed for survival every four hours for up to 96 hours. Animal health was recorded and mice were euthanized if necessary according to different clinical signs based on the mouse grimace scale recently published (41).

Statistical Analysis

Statistical analysis on mice data were generated by the Graph Pad Prism 7 for Windows (Graph Pad Software, La Jolla Calif. USA, www.araphpad.com). Tests undertaken were t test non parametric unpaired analysis (Mann-Whitney) and Log-rank test.

Example 1: The Live-Attenuated *Pseudomonas* Strain Vaccine Vector is Able to Elicit a Polyvalent Humoral Immune Response with Regard to the Pathogen *P. aeruginosa*

Figure 1B:
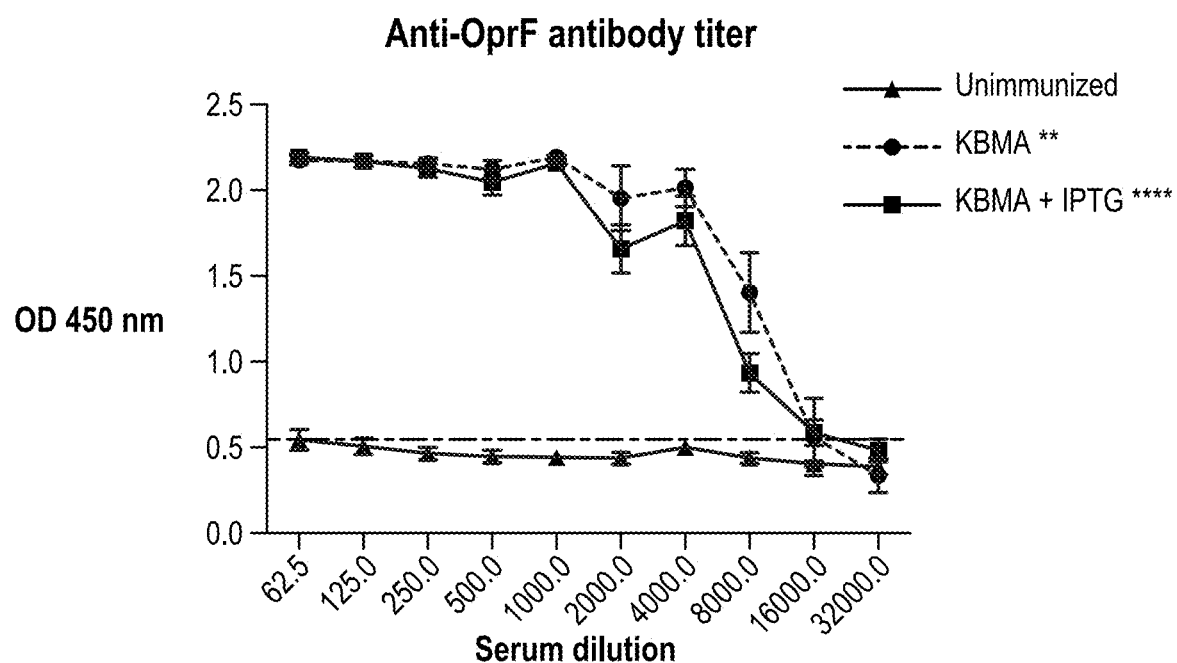

KBMA+IPTG elicited a significant anti-PcrV antibody titer (p=0.0011) compare to control (FIG. 1A), while KBMA did not (p=0.9591). KBMA and KBMA+IPTG elicited both a significant anti-OprF antibody titer (p=0.0015 and p<0.0001 respectively) compare to control (FIG. 1B). ExsA, the main activator factor of the T3SS on which is located the PcrV protein, is contained in the plasmid which transforms the vaccine strain, and is under the control of an IPTG-inducible promoter (ptaq). Thus, it is demonstrated that the addition of IPTG during the bacterial growth allows generating a specific anti-PcrV antibodies rate significantly higher. These data suggest that the addition of IPTG boosts the number of T3SS to the bacterial surface, enabling to generate a stronger humoral response against this important virulence factor and therefore against the protein PcrV, while it has no impact for the outer membrane OprF porin. As whole bacteria has been used as vaccine vector, the presentation of the different bacterial antigens to host immune cells is as natural as possible, identical to that occurs during a *P. aeruginosa* infection, which allows mice eliciting antigens-specific antibodies as natural as possible able to recognize the bacterium *P. aeruginosa* in its entirety. Furthermore, whole proteins and not just epitopes have been used to highlight antibodies, and even proteins included in a liposome as in the outer membrane of *P. aeruginosa* for the OprF porin, in order to detect at best specific antibodies elicited by this whole bacterium as vaccine vector. Thus, these coating antigens are in their most natural conformation. The average rates of anti-PcrV and anti-OprF antibodies obtained in mice were consequent, and these antibodies are only functional antibodies as they recognize conformational epitopes of PcrV and OprF naturally available. So it is demonstrated here that KBMA *P. aeruginosa* vaccine vector allows a relevant humoral immune response with regard to the pathogen *P. aeruginosa*.

Example 2: The Live-Attenuated *Pseudomonas* Strain Vaccine Vector is Able to Elicit with Regard to the Pathogen *P. aeruginosa*

A multiplex immunoassay screening for cytokines and chemokines was used to identify the different pathways of cellular response involved in mice immunized with KBMA *P. aeruginosa* vaccine vector. Cytokine and chemokine kinetics were also measured. Among the molecules analyzed, levels of IL-12p70, IL-17, GM-CSF, G-CSF, IL-5, IL-10, IL-13, TNFα, KC, MIP-1β and MCP-1 were significantly higher ($p<0.05$) at days 1 and 7 in KBMA+IPTG immunized mice than in unimmunized animals (FIG. 2). Indeed, at day 1 after the last immunization, levels of G-CSF and MIP-1β were significantly higher ($p<0.0001$) in KBMA+IPTG immunized mice than in unimmunized mice; levels of IL-17, TNFα and KC were significantly higher ($p<0.0005$) in KBMA+IPTG immunized mice than in unimmunized mice; levels of IL-13 and MCP-1 were significantly higher ($p<0.005$) in KBMA+IPTG immunized mice than in unimmunized mice; levels of IL-12p70, GM-CSF and IL-10 were significantly higher ($p<0.05$) in KBMA+IPTG immunized mice than in unimmunized mice. At day 7 after the last immunization, levels of IL-17 were significantly higher ($p<0.0001$) in KBMA+IPTG immunized mice than in unimmunized mice; levels of TNFα and MIP-1β were significantly higher ($p<0.0005$) in KBMA+IPTG immunized mice than in unimmunized mice; levels of IL-12p70, G-CSF, INFγ, IL-13, IL-1α and MCP-1 were significantly higher ($p<0.005$) in KBMA+IPTG immunized mice than in unimmunized mice; levels of GM-CSF, IL-5, IL-10, and MIP-1α were significantly higher ($p<0.05$) in KBMA+IPTG immunized mice than in unimmunized mice. At day 21, all cytokines and chemokines levels were back down at the same levels than in unimmunized mice. Therefore, it is demonstrated here that KBMA *P. aeruginosa* vaccine vector elicited several pathways of cellular response, such as Th17 (IL-17), Th1 (INFγ and IL-12) and Th2 (IL-5, IL-10, IL-13). These immunity pathways, and particularly Th17 pathway, have been shown as necessary to eradicate *P. aeruginosa* (21,22).

These results demonstrated that KBMA *P. aeruginosa* vaccine vector allows an early production of IL-17 (high rates at days 1 and 7, $p<0.0005$ and $p<0.0001$ respectively); such a response is already known to play a protective role during acute pulmonary *P. aeruginosa* infection in mice (42). Furthermore, a rationally design of the KBMA *P. aeruginosa* vaccine vector may be carried out by overexpressing beneficial effectors of Th17 pathway such as PopB protein, in order to increase this essential Th17 immune response and eradicate the pathogen. Indeed, it has been shown that PopB-immunized mice were protected from lethal pneumonia in an antibody-independent IL-17-dependent manner; and that PopB elicited an important Th17 response and also an enhanced clearance of *P. aeruginosa* from lung and spleen after challenge (25). Thus, including PopB to KBMA *P. aeruginosa* vaccine vector is a way to improve the effectiveness of the vaccine.

Thereafter, helper T cells cytokine production in spleen cells was analyzed by flow cytometry using cytokine intracellular staining assay. It is demonstrated that KBMA immunized mice produced a significantly higher rate of Th1 and Th17 helper T cells than unimmunized mice ($p<0.05$ and $p<0.0005$ respectively), but not significant for TNF a helper T cells (FIG. 3D). Unimmunized mice spleen cells co-cultured with either APCs not exposed to the bacteria or presenting KBMA antigens were not able to allow the activation of the different cellular pathways (FIG. 3E). Immunized mice spleen cells co-cultured with APCs presenting KBMA antigens elicited a significantly higher rate of Th17 and TNF a helper T cells than unimmunized mice ($p<0.005$ and $p<0.0005$ respectively), while co-cultured with APCs not exposed to the bacteria were not able to allow the activation of the different cellular pathways (FIG. 3E). These data show that KBMA *P. aeruginosa* vaccine vector is able to elicit a specific cellular immune response with several pathways such as Th17, Th1 and TNF a. Th17 pathway is particularly interesting as already shown as necessary to eradicate *P. aeruginosa* (21,22).

Example 3: Safety of Use and Easy Storage

To assess the toxicity in mice of the KBMA *P. aeruginosa* vaccine vector, the weight was followed since the first immunization to the intranasal infectious challenge. There was no significant difference (FIG. 4) in term of weight loss between KBMA+IPTG immunized mice and unimmunized mice ($p=0.4418$), although there is a slowdown in weight gain from day 21 corresponding to the establishment of immunity. Thus, this general toxicity test in mice revealed normal weight gains following 3 injections of KBMA *P. aeruginosa* vaccine. Therefore, it is demonstrated that KBMA *P. aeruginosa* vaccine vector is not toxic in mice.

Example 4: Efficacy

Three weeks after the last immunization, intranasal infectious challenges were performed on KBMA+IPTG immunized mice and unimmunized mice. With a dose of $5\times10^6$ CHU/mouse, all unimmunized mice were dead within the first 48 hours (FIG. 5), whereas the first death in immunized mice occurred at the $48^{th}$ hour after the infectious challenge. At the $150^{th}$ hour, 58.333% of immunized mice were still alive and in good health. Therefore, it is demonstrated that KBMA *P. aeruginosa* vaccine vector allows a good protective efficacy in mice, with a very significant difference compare to unimmunized mice ($p<0.0001$).

CONCLUSIONS

It is demonstrated here that KBMA *P. aeruginosa* vaccine vector is immunogenic as it elicits a broad immune response, humoral with good amount of specific antibodies particularly against PcrV protein by the adjunction of IPTG, and cellular with the activation of several pathways such as Th1, Th2 and notably Th17 pathway known as necessary to eradicate *P. aeruginosa*. It is demonstrated that this live-attenuated vaccine, which cannot replicate in its host, is very promising in term of safety of use in mice and has a protective efficacy in mice during a pulmonary infectious challenge. Furthermore, the ability to rationally design this engineered life biological product by overexpressing beneficial effectors for vaccination efficacy in order to obtain the broadest immune response as possible renders the live-attenuated *Pseudomonas* strain of the invention strongly attractive.

REFERENCES

1. Burns J L, Gibson R L, McNamara S, Yim D, Emerson J, Rosenfeld M, et al. Longitudinal Assessment of *Pseudomonas aeruginosa* in Young Children with Cystic Fibrosis. J Infect Dis. 2 janv 2001; 183(3):444-52.
2. West S E H, Zeng L, Lee B L, Kosorok M R, Laxova A, Rock M J, et al. Respiratory infections with *Pseudomonas aeruginosa* in children with cystic fibrosis: early detection by serology and assessment of risk factors. JAMA. 12 juin 2002; 287(22):2958-67.
3. Armstrong D S, Grimwood K, Carlin J B, Carzino R, Olinsky A, Phelan P D. Bronchoalveolar lavage or oropharyngeal cultures to identify lower respiratory pathogens in infants with cystic fibrosis. Pediatr Pulmonol. mai 1996; 21(5):267-75.
4. Gibson R L, Burns J L, Ramsey B W. Pathophysiology and management of pulmonary infections in cystic fibrosis. Am J Respir Crit Care Med. 15 Oct. 2003; 168(8): 918-51.
5. Alhede M, Bjarnsholt T, Givskov M, Alhede M. *Pseudomonas aeruginosa* biofilms: mechanisms of immune evasion. Adv Appl Microbiol. 2014; 86:1-40.
6. Cigana, C., N. 1. Lore, M. L. Bemardini and A. Bragonzi (2011). "Dampening Host Sensing and Avoiding Recognition in *Pseudomonas aeruginosa* Pneumonia." J Biomed Biotechnol 2011: 852513.
7. Folkesson A, Jelsbak L, Yang L, Johansen H K, Ciofu O, Helby N, et al. Adaptation of *Pseudomonas aeruginosa* to the cystic fibrosis airway: an evolutionary perspective. Nat Rev Microbiol. d6c 2012; 10(12):841-51.
8. Hassett D J, Borchers M T, Panos R J. Chronic obstructive pulmonary disease (COPD): evaluation from clinical, immunological and bacterial pathogenesis perspectives. J Microbiol Seoul Korea. mars 2014; 52(3):211-26.
9. Winstanley C, Fothergill J L. The role of quorum sensing in chronic cystic fibrosis *Pseudomonas aeruginosa* infections. FEMS Microbiol Lett. janv 2009; 290(1):1-9.
10. Strateva T, Yordanov D. *Pseudomonas aeruginosa*—a phenomenon of bacterial resistance. J Med Microbiol. sept 2009; 58(Pt 9): 1133-48.
11. Breidenstein E B M, de la Fuente-Nûrïez C, Hancock R E W. *Pseudomonas aeruginosa*: all roads lead to resistance. Trends Microbiol. août 2011; 19(8):419-26.
12. Heiby N, Ciofu 0, Bjarnsholt T. *Pseudomonas aeruginosa* biofilms in cystic fibrosis. Future Microbiol. nov 2010; 5(11):1663-74.
13. Dôrinq G, Pier G B. Vaccines and immunotherapy against *Pseudomonas aeruginosa*. Vaccine. 20 févr 2008; 26(8):1011-24.
14. Priebe G P, Goldberg J B. Vaccines for *Pseudomonas aeruginosa*: a long and winding road. Expert RevVaccines. avr2014; 13(4):507-19.
15. Worgall S. 40 years on: have we finally got a vaccine for *Pseudomonas aeruginosa*? Future Microbiol. dec 2012; 7(12):1333-5.
16. Johansen H K, Getzsche P C. Vaccines for preventing infection with *Pseudomonas aeruginosa* in cystic fibrosis. Cochrane Database Syst Rev. 2015; (8):CD001399.
17. Lin I Y C, Van T T H, Smooker P M. Live-Attenuated Bacterial Vectors: Tools for Vaccine and Therapeutic Agent Delivery. Vaccines. 10 Nov. 2015; 3(4):940-72.
18. Priebe G P. Construction and Characterization of a Live, Attenuated aroA Deletion Mutant of *Pseudomonas aeruginosa* as a Candidate Intranasal Vaccine. Infect Immun. 1 mars 2002; 70(3):1507-17.
19. Priebe G P, Meluleni G J, Coleman F T, Goldberg J B, Pier G B. Protection against Fatal *Pseudomonas aeruginosa* Pneumonia in Mice after Nasal Immunization with a Live, Attenuated aroA Deletion Mutant. Infect Immun. 1 mars 2003; 71(3):1453-61.
20. Priebe G P, Walsh R L, Cederroth T A, Kamei A, Coutinho-Sledge Y S, Goldberg J B, et al. IL-17 is a critical component of vaccine-induced protection against lung infection by lipopolysaccharide-heterologous strains of *Pseudomonas aeruginosa*. J Immunol Baltim Md 1950.1 oct 2008; 181(7):4965-75.
21. Ye P, Garvey P B, Zhang P, Nelson S, Bagby G, Summer W R, et al. Interleukin-17 and lung host defense against *Klebsiella pneumoniae* infection. Am J Respir Cell Mol Biol. September 2001; 25(3):335-40.
22. Ye P, Rodriguez F H, Kanaly S, Stocking K L, Schurr J, Schwarzenberger P, et al. Requirement of interleukin 17 receptor signaling for lung CXC chemokine and granulocyte colony-stimulating factor expression, neutrophil recruitment, and host defense. J Exp Med. 20 août 2001; 194(4):519-27.
23. Chung D R, Kasper D L, Panzo R J, Chitnis T, Grusby M J, Sayegh M H, et al. CD4+ T cells mediate abscess formation in intra-abdominal sepsis by an IL-17-dependent mechanism. J Immunol Baltim Md 1950. 15 févr 2003; 170(4):1958-63.
24. Shibata K, Yamada H, Hara H, Kishihara K, Yoshikai Y. Resident Vdelta1+gammadelta T cells contrai early infiltration of neutrophils after *Escherichia coli* infection via IL-17 production. J Immunol Baltim Md 1950. 1avr2007; 178(7):4466-72.
25. Wu W, Huang J, Duan B, Traficante D C, Hong H, Risech M, et al. Th17-stimulating protein vaccines confer protection against *Pseudomonas aeruginosa* pneumonia. Am J Respir Crit Care Med. 1 sept 2012; 186(5):420-7.
29. Hauser A R. The Type III Secretion System of *Pseudomonas aeruginosa*: Infection by Injection. Nat Rev Microbiol. sept 2009; 7(9):654-65.
30. Le Gouëllec A, Chauchet X, Polack B, Buffat L, Toussaint B. Bacterial vectors for active immunotherapy reach clinical and industrial stages. Hum Vaccines Immunother. 16 Oct. 2012; 8(10):1454-8.
31. Le Gouëllec A, Chauchet X, Laurin D, Aspord C, Verove J, Wang Y, et al. A Safe Bacterial Microsyringe for In Vivo Antigen Delivery and Immunotherapy. Mol Ther. Mai 2013; 21(5):1076-86.
35. Epaulard 0, Toussaint B, Quenee L, Derouazi M, Bosco N, Villiers C, et al. Anti-tumor Immunotherapy via Antigen Delivery from a Live Attenuated Genetically Engineered *Pseudomonas aeruginosa* Type III Secretion System-Based Vector. Mol Ther. November 2006; 14(5):656-61.
36. Quénée L, Lamotte D, Polack B. Combined sacB-based negative selection and cre-lox antibiotic marker recycling for efficient gene deletion in *Pseudomonas aeruginosa*. BioTechniques. janv 2005; 38(1):63-7.
37. Stevenson M M, Kondratieva T K, Apt A S, Tam M F, Skamene E. In vitro and in vivo T cell responses in mice during bronchopulmonary infection with mucoid *Pseudomonas aeruginosa*. Clin Exp Immunol. janv 1995; 99(1):98-105.
38. Moser C, Johansen H K, Song Z, Hougen H P, Rygaard J, Heiby N. Chronic *Pseudomonas aeruginosa* lung infection is more severe in Th2 responding BALB/c mice compared to Th1 responding C3H/HeN mice. APMIS Acta Pathol Microbiol Immunol Scand. nov 1997; 105(11):838-42.
39. Liguori L, Lenormand J L. Production of recombinant proteoliposomes for therapeutic uses. Methods Enzymol. 2009; 465:209-23.
40. Berthain L, Toussaint B, Garban F, Le Gouëllec A, Caulier B, Polack B, et al. Targeted release of transcription factors for cell reprogramming by a natural microsyringe. Int J Pharm. 20 Nov. 2016; 513(1-2):678-87.
41. Langford D J, Bailey A L, Chanda M L, Clarke S E, Drummond T E, Echols S, et al. Coding of facial expressions of pain in the laboratory mouse. Nat Methods. Juin 2010; 7(6):447-9.
42. Liu J, Feng Y, Yang K, Li Q, Ye L, Han L, et al. Early production of IL-17 protects against acute pulmonary Pseudomonas aeruginosa infection in mice. FEMS Immunol Med Microbiol. 1 mars 2011; 61(2):179-88.

The invention claimed is:

1. A method for preventively immunizing a patient against a *Pseudomonas aeruginosa* infection or for treating a patient suffering from a *Pseudomonas aeruginosa* infection, said method comprising a step of administering by injection to said patient a live-attenuated strain of *Pseudomonas aeruginosa*, the live-attenuated strain of *Pseudomonas aeruginosa*:
comprising deletion of the genes ExoS and ExoT;
expressing the gene ExsA encoding the activator of the *Pseudomonas aeruginosa* type III secretion system and the sequence encoding the 54 first amino acids of the ExoS toxin (exoS54);
expressing the protein PcrV and the protein OprF;
not being attenuated by deletion of the aroA gene; and
being treated to become killed but metabolically active by deleting the genes uvrA and uvrB encoding exonucleotidase A and B subunits, respectively, in *Pseudomonas aeruginosa* and by exposing the *Pseudomonas aeruginosa* to long wavelength UVA light in the presence of psoralen.

2. The method as claimed in claim 1, wherein said strain further expresses Orf1 (SpcS) the specific chaperone of ExoS.

3. The method as claimed in claim 1, wherein the strain further expresses at least one of the following *Pseudomonas aeruginosa* proteins: PopB, PopD, PscJ, PscI, FliC, or OprI.

4. The method as claimed in claim 1, for preventively immunizing the patient, wherein the patient has cystic fibrosis, or for treating the patient having the *Pseudomonas aeruginosa* infection, wherein the patient has cystic fibrosis.

5. A method of inducing an immune response in a patient who does not have a *Pseudomonas aeruginosa* infection or in a patient suffering from a *Pseudomonas aeruginosa* infection, the method comprising administering to said patient by injection an effective amount of a vaccine comprising:
a live-attenuated strain of *Pseudomonas aeruginosa*, the live-attenuated strain of *Pseudomonas aeruginosa*:
comprising deletion of the genes ExoS and ExoT;
expressing the gene ExsA encoding the activator of the *Pseudomonas aeruginosa* type III secretion system and the sequence encoding the 54 first amino acids of the ExoS toxin (exoS54),
expressing the protein PcrV and the protein OprF,
not being attenuated by deletion of the aroA gene, and
being treated to become killed but metabolically active by deleting the genes uvrA and uvrB encoding exonucleotidase A and B subunits, respectively, in *Pseudomonas aeruginosa* and by exposing the *Pseudomonas aeruginosa* to long wavelength UVA light in the presence of psoralen; and
a pharmaceutically acceptable carrier or adjuvant.

6. The method as claimed in claim 1, wherein the administering by injection comprises inoculating subcutaneously said live-attenuated strain of *Pseudomonas aeruginosa* to said patient.

7. The method as claimed in claim 1, wherein the administering by injection comprises administrating said live-attenuated strain of *Pseudomonas aeruginosa* to said patient by multi-position injection.

8. The method as claimed in claim 5, wherein the administering by injection comprises inoculating subcutaneously said vaccine to said patient.

9. The method as claimed in claim 5, wherein the administering by injection comprises administrating said vaccine to said patient by injection in multiple positions.

* * * * *